United States Patent
Heideman et al.

(10) Patent No.: US 10,130,791 B2
(45) Date of Patent: *Nov. 20, 2018

(54) CATHETER AND INTRODUCER CATHETER HAVING TORQUE TRANSFER LAYER AND METHOD OF MANUFACTURE

(71) Applicant: St. Jude Medical, Atrial Fibrillation Division, Inc., St. Paul, MN (US)

(72) Inventors: Wayne A. Heideman, Minnetonka, MN (US); Allen M. Fuentes, Mound, MN (US); Richard E. Stehr, Stillwater, MN (US); Sarah E. Cumming, Plymouth, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/294,424

(22) Filed: Oct. 14, 2016

(65) Prior Publication Data
US 2017/0043120 A1  Feb. 16, 2017

Related U.S. Application Data

(60) Continuation of application No. 14/989,521, filed on Jan. 6, 2016, now Pat. No. 9,492,636, which is a (Continued)

(51) Int. Cl.
*A61M 25/00* (2006.01)
*A61M 25/06* (2006.01)
(Continued)

(52) U.S. Cl.
CPC ...... *A61M 25/005* (2013.01); *A61M 25/0012* (2013.01); *A61M 25/0054* (2013.01);
(Continued)

(58) Field of Classification Search
CPC ............ A61M 25/005; A61M 25/0662; A61M 25/0012; A61M 25/0054; A61M 25/0045;
(Continued)

(56) References Cited

U.S. PATENT DOCUMENTS 4,817,613 A * 4/1989 Jaraczewski ...... A61M 25/0012
138/125
5,501,694 A  3/1996 Ressemann et al.
(Continued)

FOREIGN PATENT DOCUMENTS

EP  0839547  5/1998
EP  1712247  10/2006
(Continued)

OTHER PUBLICATIONS

International Search Report and Written Opinion for PCT/US2008/070287, dated Nov. 10, 2008.
(Continued)

*Primary Examiner* — Manuel Mendez
(74) *Attorney, Agent, or Firm* — Wiley Rein LLP (57) ABSTRACT

The instant invention relates generally to catheters and to introducer catheters used to help deliver catheters or other medical devices to locations within the human body. In particular, the instant invention relates to large diameter catheters and introducer catheters having a torque transfer layer that includes at least two flat wires braided into a wire mesh. The flat wires have a width of at least about 0.007 inches and a depth of at least about 0.003 inches. The lumen diameter of the catheter is at least about 6 French. The torque transfer layer provides increased strength, flexibility, and kink resistance.

6 Claims, 6 Drawing Sheets

Related U.S. Application Data continuation of application No. 14/097,446, filed on Dec. 5, 2013, now Pat. No. 9,259,813, which is a continuation of application No. 13/042,793, filed on Mar. 8, 2011, now Pat. No. 8,603,066, which is a division of application No. 11/779,488, filed on Jul. 18, 2007, now Pat. No. 7,914,515.

(51) Int. Cl.
| | | |
|---|---|---|
| *B23P 19/04* | (2006.01) | |
| *B29C 43/14* | (2006.01) | |
| *B29K 23/00* | (2006.01) | |
| *B29K 27/12* | (2006.01) | |
| *B29L 31/00* | (2006.01) | |

(52) U.S. Cl.
CPC .......... *A61M 25/0662* (2013.01); *B23P 19/04* (2013.01); *B29C 43/146* (2013.01); *A61M 25/0045* (2013.01); *B29K 2023/00* (2013.01); *B29K 2027/12* (2013.01); *B29L 2031/7542* (2013.01); *Y10T 29/4998* (2015.01); *Y10T 29/49826* (2015.01)

(58) Field of Classification Search
CPC .. B23P 19/04; B29C 43/146; Y10T 29/49826; Y10T 29/4998; B29K 2023/00; B29K 2027/12; B29L 2031/7542
USPC .. 604/523–532, 27, 48, 93.01, 95.01, 96.01, 604/101.01, 164.01, 164.11
See application file for complete search history.

(56) References Cited

U.S. PATENT DOCUMENTS

| | | | |
|---|---|---|---|
| 5,906,605 A | 5/1999 | Coxum | |
| 5,971,975 A | 10/1999 | Mills et al. | |
| 6,217,565 B1 | 4/2001 | Cohen | |
| 6,241,744 B1* | 6/2001 | Imran | A61B 8/0833 |
| | | | 128/898 |
| 6,511,462 B1 | 1/2003 | Itou et al. | |
| 6,582,536 B2 | 6/2003 | Shimada | |
| 7,037,290 B2 | 5/2006 | Gardeski et al. | |
| 7,914,515 B2* | 3/2011 | Heideman | A61M 25/0012 |
| | | | 604/523 |
| 8,603,066 B2 | 12/2013 | Heidman et al. | |
| 9,259,813 B2* | 2/2016 | Heideman | A61M 25/0012 |
| 9,492,636 B2* | 11/2016 | Heideman | A61M 25/0012 |
| 2002/0058910 A1 | 5/2002 | Hermann et al. | |
| 2003/0050686 A1 | 3/2003 | Raeder-Devens et al. | |
| 2003/0236492 A1 | 12/2003 | Honebrink | |
| 2004/0060944 A1 | 4/2004 | Gervasi | |
| 2004/0111095 A1* | 6/2004 | Gordon | A61B 17/3468 |
| | | | 606/108 |
| 2004/0122360 A1 | 6/2004 | Waldhauser et al. | |
| 2004/0153049 A1* | 8/2004 | Hewitt | A61M 25/0012 |
| | | | 604/527 |
| 2004/0236346 A1 | 11/2004 | Parker | |
| 2006/0229589 A1 | 10/2006 | Itou et al. | |
| 2007/0006944 A1 | 1/2007 | Waseda et al. | |
| 2007/0060944 A1 | 3/2007 | Boldenow et al. | |
| 2007/0255255 A1* | 11/2007 | Shah | A61M 25/0012 |
| | | | 604/527 |
| 2009/0143633 A1 | 6/2009 | Edmundson et al. | |
| 2014/0336572 A1 | 11/2014 | Heisel et al. | |
| 2015/0005704 A1 | 1/2015 | Heisel et al. | |

FOREIGN PATENT DOCUMENTS

| | | |
|---|---|---|
| EP | 2471480 | 7/2012 |
| JP | H04319365 | 11/1992 |
| JP | H10043300 | 2/1998 |
| JP | H11000401 | 6/1999 |
| JP | H11155956 | 6/1999 |
| JP | H11509751 | 8/1999 |
| JP | 2000126301 | 5/2000 |
| JP | 2001501846 | 2/2001 |
| JP | 200187389 | 4/2001 |
| JP | 2003514633 | 4/2003 |
| JP | 2006513774 | 4/2006 |
| JP | 2006288670 | 10/2006 |
| WO | 9701369 | 1/1997 |
| WO | 9815311 | 4/1998 |
| WO | 0137918 | 5/2001 |
| WO | 2004058341 | 7/2004 |
| WO | 2007136981 | 11/2007 |

OTHER PUBLICATIONS

International Search Report and Written Opinion for PCT/US2014/037137, dated Aug. 27, 2014.

* cited by examiner

CATHETER AND INTRODUCER CATHETER HAVING TORQUE TRANSFER LAYER AND METHOD OF MANUFACTURE

CROSS-REFERENCE TO RELATED APPLICATIONS

This application is a continuation of U.S. application Ser. No. 14/989,521, filed 6 Jan. 2016, now pending, which is a continuation of U.S. application Ser. No. 14/097,446, filed 5 Dec. 2013, now U.S. Pat. No. 9,259,813, which is a continuation of U.S. application Ser. No. 13/042,793, filed 8 Mar. 2011, now U.S. Pat. No. 8,603,066, which is a divisional of U.S. application Ser. No. 11/779,488, filed 18 Jul. 2007, now U.S. Pat. No. 7,914,515. Each of the foregoing is hereby incorporated by reference in its entirety as though fully set forth herein.

BACKGROUND OF THE INVENTION a. Field of the Invention

The instant invention relates generally to catheters and to introducer catheters used to help deliver catheters or other medical devices to locations within the human body. In particular, the instant invention relates to catheters and introducer catheters having a torque transfer layer configured to provide increased strength, flexibility, and kink resistance.

b. Background Art

Catheters are used for an ever growing number of medical procedures. To name just a few examples, catheters are used for diagnostic, therapeutic, and ablative procedures. Typically, the physician manipulates the catheter through the patient's vasculature to the intended site, such as a site within the patient's heart. The catheter typically carries one or more electrodes or other diagnostic or therapeutic devices, which may be used for ablation, diagnosis, cardiac mapping, or the like.

It is known that, to facilitate placement of the diagnostic or therapeutic catheter at a location of interest within the patient, it may be introduced through another catheter, commonly known as a "guiding catheter" or "introducer catheter," and the terms will be used interchangeably herein. Generally speaking, an introducer catheter is a tube having a high degree of directional control that is used to place other catheters, which may have little or no directional control, into specific areas of the patient's body.

In the field of cardiac ablation, for example, introducer catheters may be used to negotiate the patient's vasculature such that an ablation device may be passed therethrough and positioned to ablate arrhythmia-causing cardiac tissue. The introducer catheter itself may be advanced over a guide wire.

Generally, it is known that the introducer catheter must have an overall diameter small enough to negotiate blood vessels while retaining an inner diameter (or "bore size") large enough to accommodate the ablation device therethrough. Furthermore, since the path within the patient is often long and tortuous, steering forces must be transmitted over relatively great distances. Accordingly, it is desirable for the introducer catheter to have sufficient axial strength to be pushed through the patient's vasculature via a force applied at its proximal end ("pushability"). It is also desirable for the introducer catheter to transmit a torque applied at the proximal end to the distal end ("torqueability"). An introducer catheter should also have sufficient flexibility to substantially conform to the patient's vasculature and yet resist kinking as it does so. One of ordinary skill in the art will recognize that these various characteristics are often in tension with one another, with improvements in one requiring compromises in others. For example, increasing the bore size of an introducer catheter having a given overall diameter requires utilizing a thinner wall. A thin-walled introducer, however, is more likely to collapse upon itself when a torque is applied at its proximal end.

To improve pushability, torqueability, flexibility, and kink resistance, many extant introducer catheters utilize one or more reinforcing layers in their construction. For example, the guiding catheter disclosed in U.S. Pat. No. 4,817,613 to Jaraczewski et al. ("Jaraczewski") includes a pair of braided torque transmitting layers sandwiched between a flexible tubular member and a flexible plastic casing applied as a viscous material and subsequently cured. Jaraczewski also teaches, however, that to a certain degree, flexibility comes at the expense of torqueability. Further, depending on the thickness of the torque transfer layers, they may increase the wall thickness, thereby either increasing the overall diameter of the introducer catheter for a given bore size or decreasing the bore size for a given overall diameter.

Many extant large bore introducers (i.e., an introducer catheter with bore size of greater than about 6 French), in order to find a suitable balance of pushability, torqueability, flexibility, and kink resistance, have outer layers that are relatively stiff, which compromises torqueability, kink resistance, and flexibility for pushability.

BRIEF SUMMARY OF THE INVENTION

Embodiments of the present invention provide a catheter, particularly an introducer catheter, having good pushability, torqueability, flexibility, and kink resistance, while retaining a large bore size for a given overall diameter. In specific embodiments, an introducer catheter with good pushability, torqueability, flexibility, and kink resistance has a bore size of at least about 6 French and an overall diameter suitable for use in cardiac diagnostic and therapeutic procedures. The invention further provides a method of constructing a catheter or an introducer catheter that does not require compromising some of the characteristics of pushability, torqueability, flexibility, and kink resistance for others of those characteristics.

In accordance with an aspect of the present invention, a catheter or an introducer catheter for cardiac surgery comprises a tubular inner liner, a torque transfer layer, or reinforcing layer, surrounding at least a portion of the inner liner, the torque transfer layer comprising at least two flat wires braided into a wire mesh, and an outer sheath formed over to the torque transfer layer. The flat wires are substantially rectangular in cross-section and have a width of at least about 0.007 inches and a depth of at least about 0.003 inches. The tubular inner liner has a lumen diameter of at least about 6 French.

In specific embodiments, the catheter is an introducer catheter. The tubular inner liner is polymeric and the outer sheath comprises a melt-processing polymer. The ratio of width to thickness of the introducer catheter may be between about 2:1 and about 5:1. The torque transfer layer has a braid density of between about 5 PPI and about 100 PPI and may be braided in a one-over, one-under pattern, or a two-over, two-under pattern. The outer sheath comprises a plurality of segments having differing hardness characteristics, and the segments are reflow bonded together.

In accordance with another aspect of the invention, a method of manufacturing a catheter of an introducer catheter for cardiac surgery comprises forming a tubular inner liner about a mandrel, the liner having a proximal end, a distal end, a lumen diameter of at least about 6 French; forming a torque transfer layer over at least a portion of the liner, the torque transfer layer comprising a plurality of braided flat wires, the flat wires being substantially rectangular in cross-section and having a width of at least about 0.007 inches and a depth of at least about 0.003 inches: forming an outer sheath about the torque transfer layer; and removing the mandrel. In specific embodiments, the tubular inner liner is polymeric and the outer sheath comprises a melt-processing polymer. The method further comprises heating the inner liner, torque transfer layer, and outer sheath to a temperature sufficient to melt the melt-processing polymer.

The foregoing and other aspects, features, details, utilities, and advantages of the present invention will be apparent from reading the following description and claims, and from reviewing the accompanying drawings.

DETAILED DESCRIPTION OF THE INVENTION

The present invention provides a catheter and a large bore introducer catheter suitable for use in the human vasculature for known medical procedures, such as cardiac ablation. For purposes of description, the present invention will be described in connection with a flat wire guided, or steerable, introducer catheter. It is contemplated, however, that the described features may be incorporated into any number of catheters or introducer catheters as would be appreciated by one of ordinary skill in the art. The large bore introducer catheter is comprised of a combination of components and manufactured by either a reflow process or an extrusion process, which provide the surprising benefits of allowing for introducer catheters having an internal diameter of at least about 6 French while maintaining the desirable improved properties of pushability, torqueability, and flexibility, for outer diameters of sufficient size for navigation of cardiac vasculature.

Figure 1:
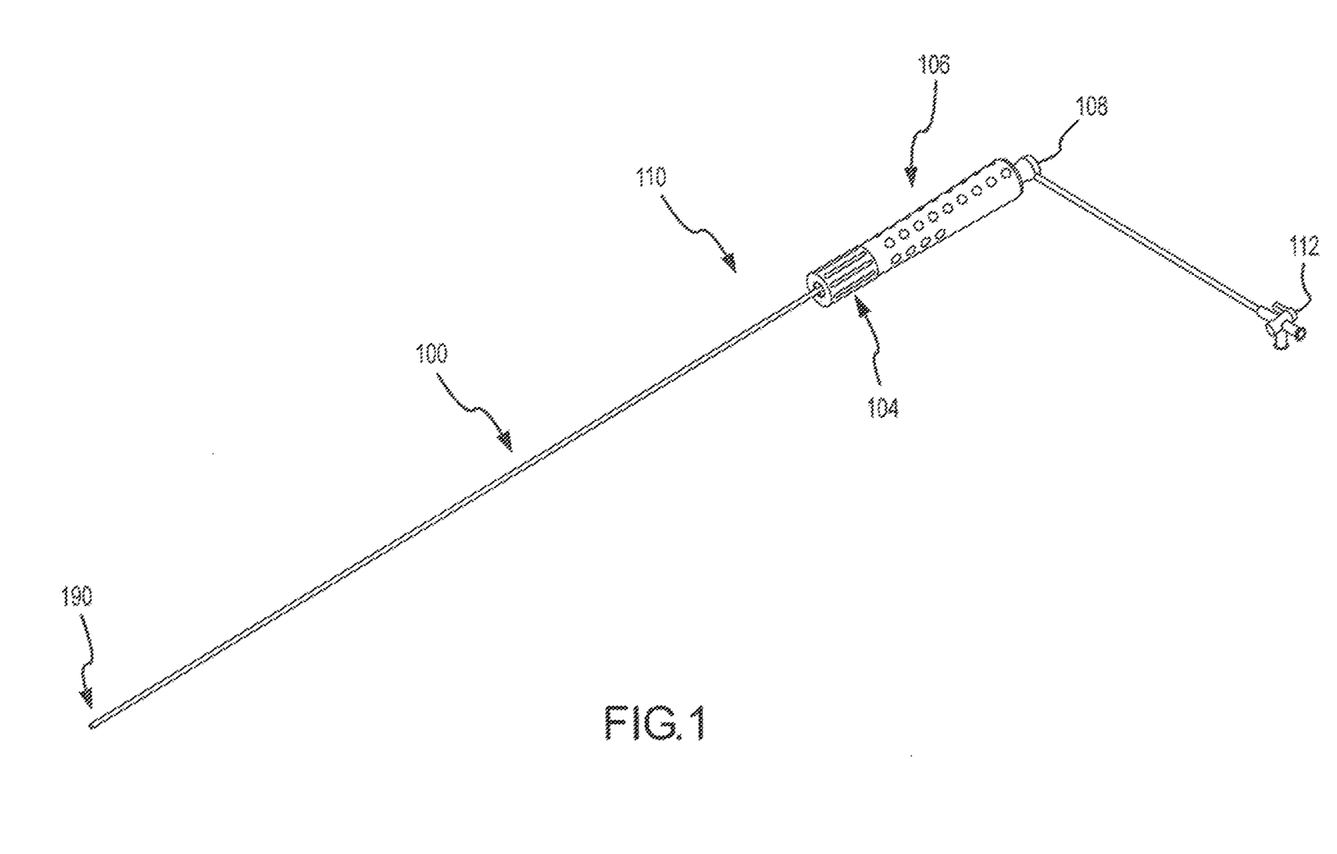
FIG. 1 is a perspective view of an introducer assembly in accordance with one embodiment of the present invention.

FIG. 1 is a perspective view of an introducer assembly 110 according to one embodiment of the present invention comprising an introducer catheter 100 having a distal end 190 and a proximal end 104. The introducer catheter 100 may be operably connected to a handle assembly 106 which assists in guiding or steering the introducer during procedures. The introducer assembly 110 further includes a hub 108 operably connected to an inner lumen (not shown) within the handle assembly 106 for insertion or delivery of catheter assemblies, fluids, or any other devices known to those of ordinary skill in the art. Optionally, the introducer assembly 110 further includes a valve 112 operably connected to the hub 108.

Figure 2:
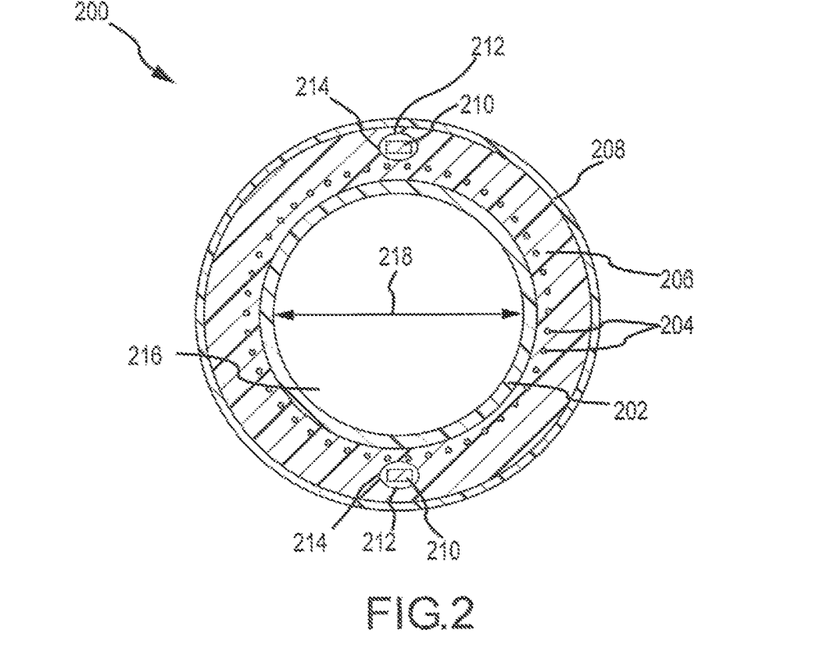
FIG. 2 is a cross-sectional view of a steerable, large bore introducer in accordance with another embodiment of the present invention.

FIG. 2 depicts a cross-sectional view of an introducer catheter 200 in accordance with one embodiment of the present invention. The introducer catheter 200 is comprised of a tubular polymeric inner liner 202, a torque transfer layer 204, an outer sheath 206 comprised of a melt-processing polymer, and a heat shrink layer 208. In the instance where the introducer is a steerable introducer, the introducer catheter 200 further includes at least one flat wire 210 disposed longitudinally along the length of the introducer catheter 200. For purposes of this invention, a "flat wire" refers to a wire that is characterized by a cross-section that, when measured along two orthogonal axes, is substantially flat. A flat wire typically has a rectangular cross section, though the cross section need not be perfectly rectangular. For example, the present invention contemplates that a cross section of the flat wire may be oval, provided that the overall cross section is generally flat. As the term is used herein, a wire may be properly characterized as a flat wire if it has a cross section that is measured x in one direction and at least 2x in a second direction generally orthogonal to the first direction. A wire whose cross section is substantially I-shaped may also be a flat wire if, generally, its height is substantially greater than its width at its widest measurement. One of ordinary skill will appreciate that a flat wire may be defined in the context of the overall teachings of this application.

The at least one flat wire 210 may be further encased inside another polymeric tubular member 212 forming a lumen 214 for housing the flat wire 210. The introducer catheter according to this embodiment is manufactured by a reflow bonding process in which the components are individually fed over a mandrel as discussed in more detail below.

The inner liner 202 is preferably a polymeric material, such as polytetrafluoroethylene (PTFE) or etched PTFE. The inner liner 202 may also be made of other melt processing polymers, including, without limitation, polyether block amides, nylon and other thermoplastic elastomers. Once such elastomer is Pebax® made by Arkema, Inc. Pebax of various durometers may also be used, including without limitation, Pebax 30D to Pebax 70D. In a preferred embodiment, the inner liner 202 is made of a material with a melting temperature higher than the outer sheath 206 such that the inner liner 202 will withstand the melt processing of the outer sheath 206.

Inner liner 202 defines a lumen 216 therethrough, preferably having a diameter 218 of at least about 6 French, more preferably of at least about 7 French, and most preferably of between about 10 French and about 24 French. However, in some embodiments of the invention, it is contemplated that lumen 216 may have a diameter 218 of up to about 32 French or more, such as between about 7 French and about 32 French.

A torque transfer layer 204 is preferably disposed between the inner liner 202 and the heat shrink layer 208, more preferably between the outer sheath 206 and the inner liner 202. In the instance where the introducer is a steerable introducer utilizing, for example, at least one longitudinal wire 210, the torque transfer layer 204 may be disposed between either the inner layer 202 and the outer sheath 206 or the outer sheath 206 and the heat shrink layer 208. The torque transfer layer 204 may be made of stainless steel (304 or 316) wire or other acceptable materials known to those of ordinary skill in the art.

The torque transfer layer 204 is preferably formed of a braided wire assembly comprised of flat wires, preferably stainless steel wires including, for example, high tensile stainless steel wires. The torque transfer layer 204 may be formed in any number of known braid patterns, including one-over-one (involving at least two wires) or two-over-two (involving at least four wires) crossover patterns. For lumen diameters of at least about 6 French, braided flat wires of at least about 0.003" thick by at least about 0.007" wide, which heretofore were not used to form a wire mesh for the torque transfer layer, have produced surprisingly good results of increased pushability, torqueability, flexibility, and kink resistance over non-flat wires and smaller flat wires. In general, the individual wires have a ratio of width to the thickness of at least about 2:1, including, for example, 2:1 to 5:1. Flat wires of about 0.004" thick by about 0.012" wide and of about 0.004" thick by about 0.020" wide have also been braided with success to form torque transfer layers of superior performance.

The braid density, commonly measured in pixels per inch ("PPI"), is typically between about 5 and 100, and will depend on the size of the flat wires as well as the size of the catheter. For flat wires of at least about 0.003" thick by about 0.007" wide and a catheter having an inner lumen of at least about 6 French, the PPI is preferably between about 10 and about 90, more preferably between about 10 and about 55. For example, the PPI for flat wires of about 0.003" thick by about 0.007" wide is preferably between about 20 and about 90, more preferably between about 35 and about 55 for an inner lumen of at least 6 French, and most preferably between about 35 and about 45 for an inner lumen of at least about 10 French. The PPI for flat wires of about 0.004" thick by about 0.012" wide is preferably between about 15 and about 70, and more preferably between about 15 and about 22 for all inner lumen of at least about 6 French. The PPI for flat wires of about 0.004" thick by about 0.020" wide is preferably between about 5 and about 50, and more preferably between about 10 and about 20 for an inner lumen of at least about 6 French, and most preferably between about 10 and about 20 for an inner lumen of at least about 16 French.

Alternatively, the torque transfer layer 204 may utilize a varying braid density construction along the length of the introducer catheter 200. For example, the torque transfer layer may be characterized by a first braid density at the proximal end of the introducer catheter 200 and then transition to one or more braid densities as the torque transfer layer 204 approaches the distal end of the introducer catheter 200; the braid density of the distal end may be greater or less than the braid density at the proximal end. In a specific example, the braid density at the proximal end is about 50 PPI and the braid density at the distal end is about 10 PPI. In another embodiment, the braid density at the distal end is about 20-35% of the braid density at the proximal end.

The torque transfer layer 204 may be formed separately on a disposable core and subsequently slipped around the inner liner 202. One or more portions of the torque transfer layer 204 may be heat tempered and cooled before incorporation into the introducer body 200 through methods that are known to those of ordinary skill. The action of heat tempering may help to release the stress on the wire and help reduce radial forces. It is also contemplated that torque transfer layer 204 may be braided directly on the inner liner 202.

A particularly preferred torque transfer layer 204 is comprised of 0.003" by 0.007" 304 stainless steel wires at 35 PPI for an inner lumen of 6-10 French. Another preferred torque transfer layer 204 is comprised of 0.004" by 0.012" 304 stainless steel wires at 22 PPI for an inner lumen of 12 French. Yet another preferred torque transfer layer 204 is comprised of 0.004" by 0.020" 304 stainless steel wires at 13 PPI for an inner lumen of 16 French. These particularly preferred torque transfer layers may manufactured on a commercially available horizontal braid machine set at 225 rpm utilizing a commercially available mandrel. Other suitable methods of manufacturing the torque transfer layer 204 will be apparent to those of ordinary skill in the art.

Figure 6:
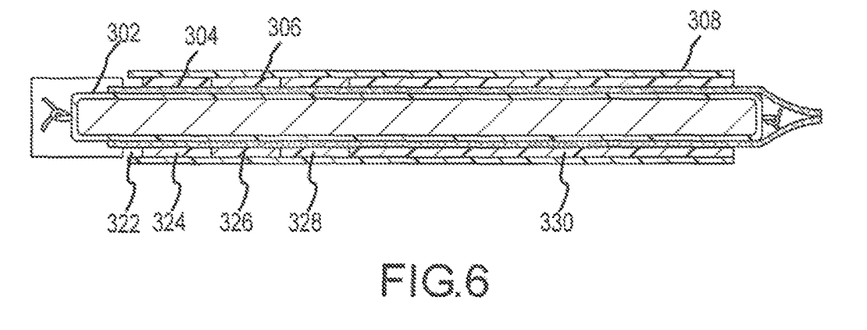
FIG. 6 depicts an outer sheath of varying components disposed over a torque transfer layer in accordance with a preferred method of manufacture.

The outer sheath 206 is preferably either an extruded Pebax or PTFE tubing. The melt-processing polymer of the outer sheath 206 occupies a plurality of voids of the wire mesh in the torque transfer layer. The outer sheath 206 may also be made of other melt processing polymers, including, without limitation, etched PTFE, polyether block amides, nylon and other thermoplastic elastomers, at varying durometers. The outer sheath 206 may also comprise more than one layer, including, for example, two or more tubes of a melt processing polymer. Alternatively, as shown in FIG. 6, the outer sheath 306 may be comprised of varying segments 322, 324, 326, 328, 330 differing in hardness and/or material along the length of the introducer 300 and being reflow bonded together. This may be accomplished by layering or by placing annular rings of differing materials along the length of the introducer 300. Varying the sheath composition in this manner provides the additional benefit of adjusting flexibility, torqueability, and pushability at various points along the introducer 300.

Figure 10:
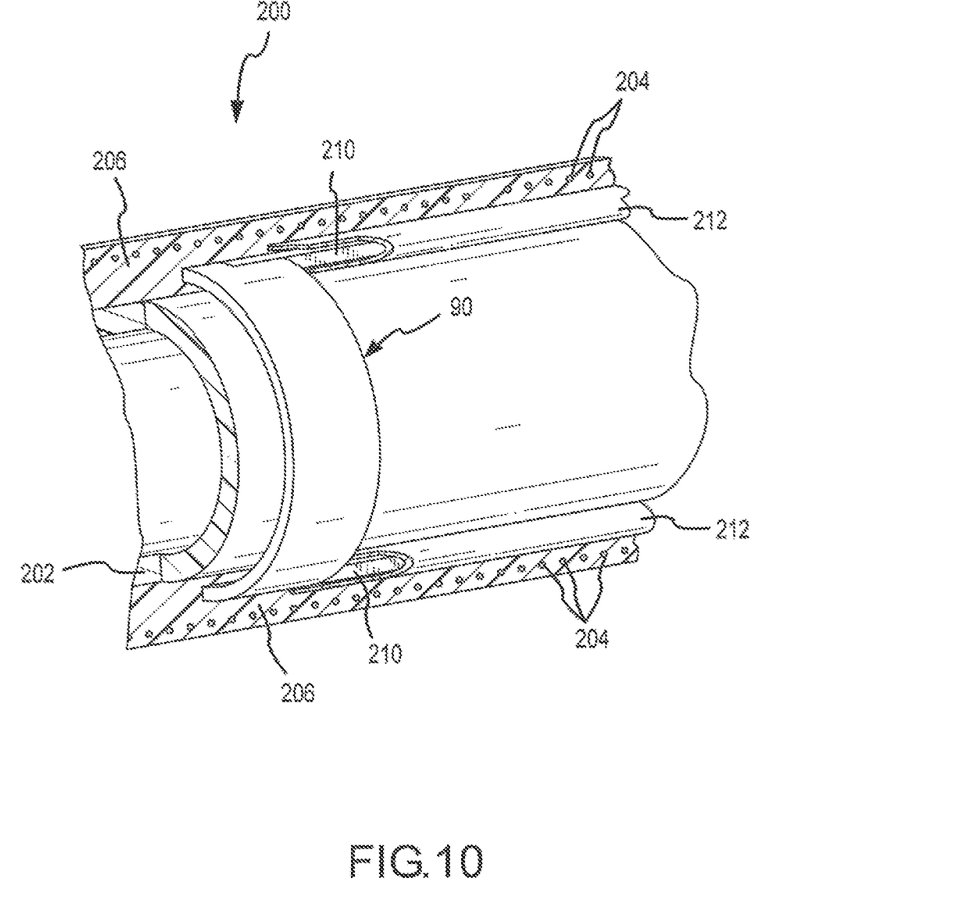
FIG. 10 is a perspective view of a steerable introducer in accordance with an embodiment of the present invention, cut away to show details of the steering ring.

In embodiments where the introducer is a steerable introducer (as shown in FIG. 2), at least one flat wire 210 is provided, preferably extending along substantially the entire length of the introducer. The flat wire 210 is preferably composed of stainless steel and is preferably about 0.002" by about 0.016", and more preferably about 0.004" by about 0.012" or 0.016". The flat wire may be selected such that the ratio of the width to thickness is at least about 2:1. In one embodiment, at least a portion of the flat wire is encased inside a preformed tube 212 before placement along the inner liner 202 to form a flat lumen 214. The preformed tube 212 need not be the same shape as the cross section of the flat wire, but instead, may be round, oval, rectangular, or another like shape. Preferably, the preformed tube 212 has a cross section that is not the same shape as a cross section of the flat wire 210, in order to facilitate movement of the flat wire in the preformed tube. The preformed tube may be formed of PTFE, etched PTFE, polyether block amides (such as Pebax), nylon, other thermoplastic elastomers, or any other known material to one of ordinary skill in the art. Preferably, the preformed tube 212 has a higher melting point than the outer sheath 206 so that the preformed tube 212 will not melt when the introducer catheter 200 is subjected to melt processing. In alternative embodiments the flat wire 210 may be covered with lubricious materials (not shown) before placement, including silicone and other lubricious materials. Alternatively, the flat wire 210 may also be coated with a lubricious layer to promote slidability, and it is also contemplated that the flat wire 210 may be manufactured with a smooth surface to promote slidability. While stainless steel is a preferred material to compose the flat wire 210, other materials may be used, including, without limitation, materials that are used for conventional round pull wires. More than one flat wire 210 may also be used, and in such cases, each such flat wire 210 may be encased inside its own flexible tube 212. Preferably, as shown in FIG. 2, a pair of flat wires 210 are used that are spaced at 180 degrees apart. The flat wires 210 are preferably connected to at least one steering ring 90 typically located near the distal end of the introducer (see, e.g., FIG. 10). The proximal ends of the flat wires 210 are then operably connected to a steering mechanism (not shown) allowing for manipulation, or steering, of the introducer catheter 200 during use. FIG. 10 shows a cutaway view of the introducer catheter 200 according to the present invention highlighting the steering ring 90 and its connection to the pull wires 210.

Figure 3:
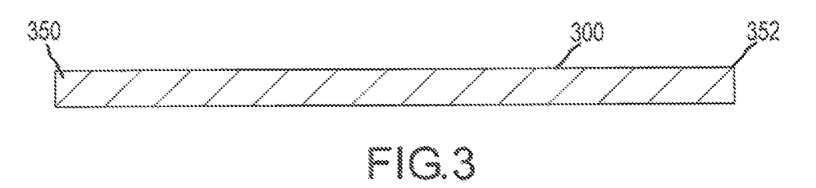
FIG. 3 depicts a reflow mandrel assembly used in the method of manufacturing introducers in accordance with the present invention.
Figure 4:
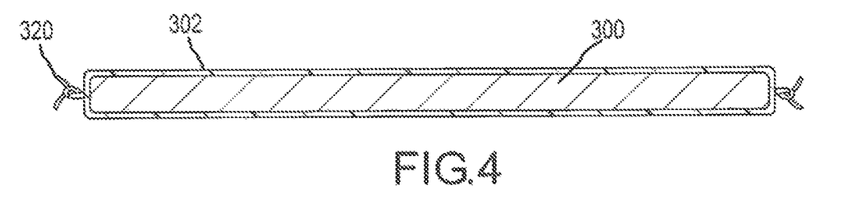
FIG. 4 depicts an inner layer disposed over a reflow mandrel assembly in accordance with a preferred method of manufacture.

The basic method of manufacture according to an embodiment of the present invention will be described in reference to FIGS. 3-9. As the various components are assembled, the introducer components will be collectively referred to as an introducer. As depicted in FIGS. 3-9, a mandrel 300, which is preferably round in cross-section and preferably from about 6 inches to about 4 feet in length, is provided. As depicted in FIG. 3, the mandrel 300 has a distal end 350 and a proximal end 352. As depicted in FIG. 4, an inner liner 302 is placed on the mandrel 300. The inner liner 302 is fed on to the mandrel 300 and is then knotted on one end 320, or both ends.

Figure 5:
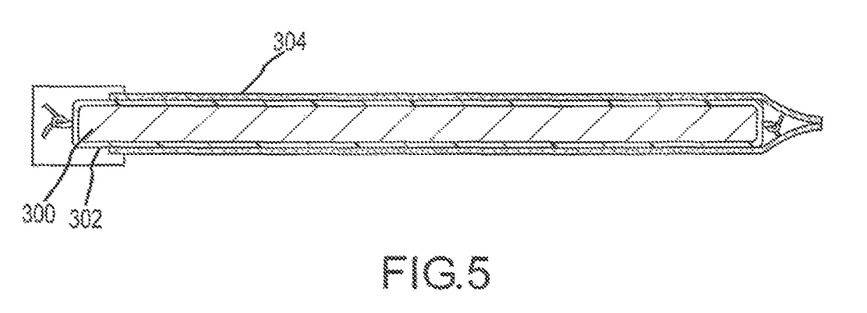
FIG. 5 depicts a torque transfer layer disposed over an inner layer in accordance with a preferred method of manufacture.

As depicted in FIG. 5, a torque transfer layer 304 is then placed over the inner liner 302. In the case of a steerable introducer catheter, the flat wire assembly (not shown) may then be placed over the torque transfer layer 304. Alternatively, the flat wire assembly may be placed over an outer sheath 306. Another sheath layer (not shown) may additionally be placed over the flat wire assembly. The torque transfer layer terminates proximally of the distal end of the catheter.

Next, as depicted in FIG. 6, an outer sheath 306 is placed over the torque transfer layer 304 and may be made of either single or multiple sections of tubing that are either butted together or overlapped with each other. The multiple segments, or layers, of sheath material may be any length and/or hardness (durometer) allowing for flexibility of design. FIG. 6 identifies a plurality of segments, 322, 324, 326, 328 and 330. In this embodiment, the proximal end 330 of the outer sheath 306 may be made of a material such as nylon, and the remainder of the introducer may be made of one or more Pebax materials. The lengths of the various segments may vary, but preferably, the durometer hardness levels will decrease as the outer sheath 306 approaches its distal end. For example, a nylon base may then be followed by one or more of the following Pebax segments: 70D Pebax; 60D Pebax; 55D Pebax; 40D Pebax; 35D Pebax; 30D Pebax. The introducer shaft may also use one or more blends of the foregoing Pebax materials, including, for example, 70D/60D Pebax blend made by co-extrusion, or a 40D/35D Pebax blend made by co-extrusion. Preferably, the various components of the outer sheath 306 according to this embodiment will be reflowed together during manufacturing. The proximal end of the shaft is preferably the longest segment, and more distal segments may preferably vary between 0.25" to 6", and more preferably from 0.25" to about 3". Preferably, the hardness levels of the segments and the lengths of the segments may be adjusted for specific applications, and preferably, the distal end may have the lowest durometer levels of all segments. The shaft segments may be selected to improve flexibility, torqueability, and pushability for the specific application, as appreciated by one of ordinary skill in the art. Alternatively, the catheter may be formed by placing a thin inner jacket or layer (e.g., PTFE layer) onto a mandrel (e.g., stainless steel mandrel) or extruding a thin inner jacket or layer (e.g., Pebax layer) onto an extrusion mandrel (e.g., acetal mandrel), forming a torque transfer layer over the inner layer, and extruding an outer jacket or sheath (e.g., Pebax jacket) over the torque transfer layer.

Lastly, a heat shrink layer 308 is placed over the assembled introducer assembly prior to reflow lamination. The heat shrink layer 308 is preferably a fluoropolymer or polyolefin material, such as FEP, or other suitable material as appreciated by one of ordinary skill in the art.

After assembly of the various components, the introducer assembly 300 is subjected to a reflow lamination process. FIG. 2 depicts a cross sectional view of the introducer assembly after this reflow process. Introducer assembly 200 may be laminated by heating the assembly until the material comprising the outer sheath 206 flows and redistributes around the circumference. Preferably, the heat shrink layer 208 has a higher melt temperature than the outer sheath 206, and during the melt process, the heat shrink layer 208 retains its tubular shape and forces the liquefied sheath layer material 206 into the torque transfer layer 204 and into contact with the flat wires 210/preformed tubes 212 (if present) and the inner liner 202. The introducer assembly 200 may then be cooled. The mandrel is preferably left in place during the cooling process as it helps the introducer assembly to retain its inner lumen of at least about 6 French. The heat shrink layer 208 may be left on the introducer assembly 200, or optionally removed. If the heat shrink layer 208 is removed, the outer sheath 206 becomes the outside layer of the introducer catheter 200.

Figure 7:
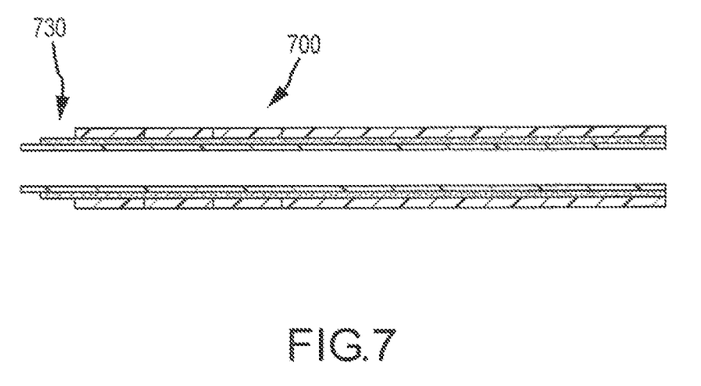
FIG. 7 depicts the components of an introducer assembled over a reflow mandrel assembly having a distal configuration for a tip assembly.
Figure 8:
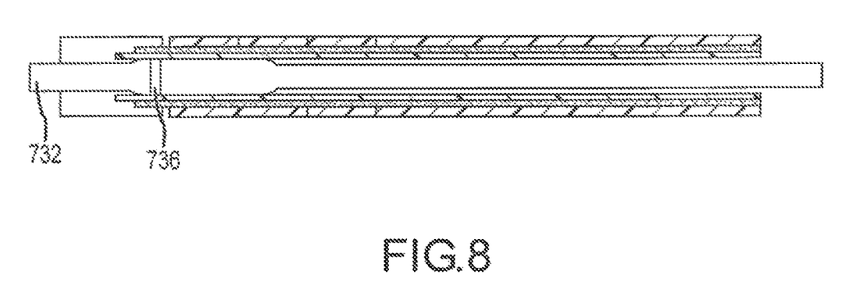
FIG. 8 depicts a tip component, having a radiopaque marker, attached to the distal end of the introducer depicted in FIG. 7.
Figure 9:
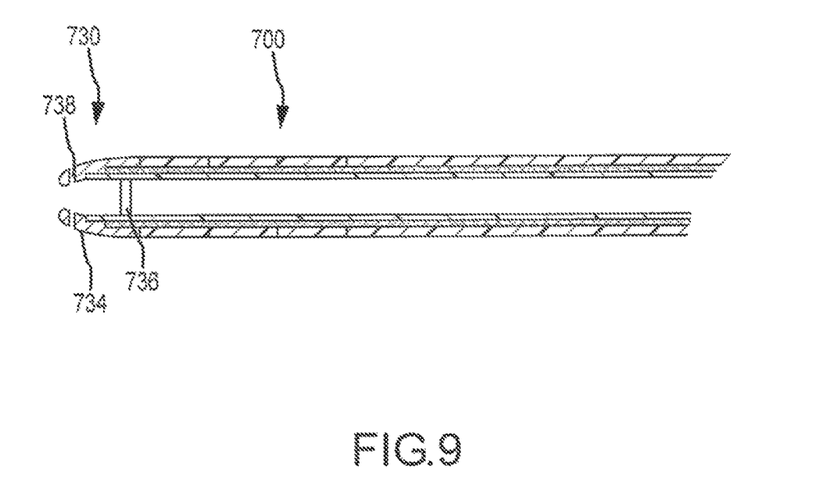
FIG. 9 depicts another tip component, having a radiopaque marker, attached to the distal end of the introducer depicted in FIG. 7.

Additionally, as shown in FIGS. 7-9, the present invention contemplates the inclusion of a tip assembly for use in medical procedures, such as an atraumatic tip, including, for example, a radiopaque material contained therein for location of the tip during use. For example, FIGS. 7-9 depict a cross section of an introducer catheter 700 having a distal portion 730 configured to accept a tip assembly 732 or 734. In both examples, the tip 732 or 734 includes a ring 736, e.g., a radiopaque marker, for location of the tip 732 or 734 during use. Additionally, FIG. 9 further includes a tip assembly 734 configured with a plurality of port holes 738 for delivery of, for example, irrigation fluid. The tip assembly may further be configured with ablation electrodes (not shown) operably connected to a power supply (not shown), for use in cardiac ablation procedures.

Although several embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A catheter shaft having a proximal end and a distal end, the catheter shaft comprising:
    a lumen surrounded by an inner liner, a torque transfer layer, and an outer sheath,
    wherein the torque transfer layer comprises a braided wire assembly having a proximal portion and a distal portion, wherein the braided wire assembly has a first density at the proximal portion and a second density at the distal portion, and
    wherein the first density differs from the second density, and further wherein the braided wire assembly comprises at least two flat wires;
    wherein the outer sheath comprises a plurality of segments having varying hardness; and
    wherein the torque transfer layer is disposed between the inner liner and the outer sheath.

2. The catheter shaft of claim 1, wherein the diameter of the lumen is at least 6 French.

3. The catheter shaft of claim 1, wherein the pixels per inch (PPI) for the flat wires is between about 20 and about 90.

4. The catheter shaft of claim 1, wherein the PPI at the proximal portion of the braided wire assembly is greater than the PPI at the distal portion of the braided wire assembly.

5. The catheter shaft of claim 1, wherein at least one flat pull wire is disposed longitudinally between the distal end and the proximal end of the catheter shaft.

6. The catheter shaft of claim 5, wherein the at least one flat pull wire is operably connected to a steering mechanism.

* * * * *